(12) United States Patent
Bracht

(10) Patent No.: US 7,468,470 B2
(45) Date of Patent: Dec. 23, 2008

(54) MEDICINAL PATCH THAT LEAVES LESS ADHESIVE RESIDUE WHEN REMOVED

(75) Inventor: Stefan Bracht, Jena Cospeda (DE)

(73) Assignee: Schering AG, Berlin (DE)

(*) Notice: Subject to any disclaimer, the term of this patent is extended or adjusted under 35 U.S.C. 154(b) by 329 days.

(21) Appl. No.: 11/089,935

(22) Filed: Mar. 25, 2005

(65) Prior Publication Data
US 2005/0215934 A1 Sep. 29, 2005

Related U.S. Application Data

(60) Provisional application No. 60/558,033, filed on Mar. 31, 2004.

(51) Int. Cl.
*A61F 13/00* (2006.01)

(52) U.S. Cl. .............. 602/48; 602/41; 602/52; 602/57

(58) Field of Classification Search ............. 602/41–59, 602/600; 128/888, 889
See application file for complete search history.

(56) References Cited

U.S. PATENT DOCUMENTS

| | | | |
|---|---|---|---|
| 3,366,112 A * | 1/1968 | Antonik | 604/306 |
| 4,664,106 A | 5/1987 | Snedeker | |
| 4,753,232 A | 6/1988 | Ward | |
| 5,310,402 A * | 5/1994 | Rollband | 602/42 |
| 5,533,962 A * | 7/1996 | Peterman et al. | 602/54 |
| 5,599,289 A | 2/1997 | Castellana | |
| 5,690,610 A | 11/1997 | Ito et al. | |
| 5,939,339 A * | 8/1999 | Delmore et al. | 442/149 |

FOREIGN PATENT DOCUMENTS

| | | |
|---|---|---|
| DE | 204946 | 12/1908 |
| DE | 743 775 | 3/1944 |
| EP | 1 062 926 A1 | 12/2000 |
| EP | 0 614 652 B1 | 7/2001 |
| JP | 9010256 | 1/1997 |
| WO | 95/05827 | 3/1995 |
| WO | 97/03709 | 2/1997 |

* cited by examiner

*Primary Examiner*—Kim M Lewis
(74) *Attorney, Agent, or Firm*—Michael J. Striker

(57) ABSTRACT

The medicinal patch for delivering a pharmaceutically effective ingredient by contact with skin has a backing layer (1), an effective-ingredient containing adherent layer (2) on the backing layer and a release layer (4) applied over the adherent layer (2). To eliminate a dirt ring deposited when the medicinal patch is finally removed from the skin, a plastic foil or film (3) is provided on an outer peripheral or edge region of the skin-contacting surface of the adherent matrix layer (2). The plastic foil or film, which does not adhere to the skin, can be made of polyester, hydrocarbon polymers or silicone polymers and preferably has a thickness of 15 to 75 μm with a width of 1 to 3 mm. Methods of making medicinal patches of this sort are described.

5 Claims, 2 Drawing Sheets

FIG. 5
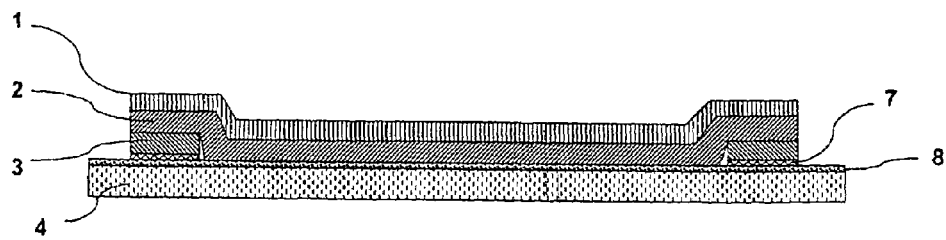
FIG. 6
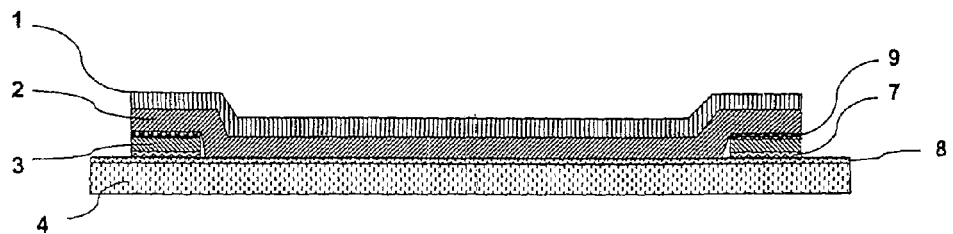
FIG. 7
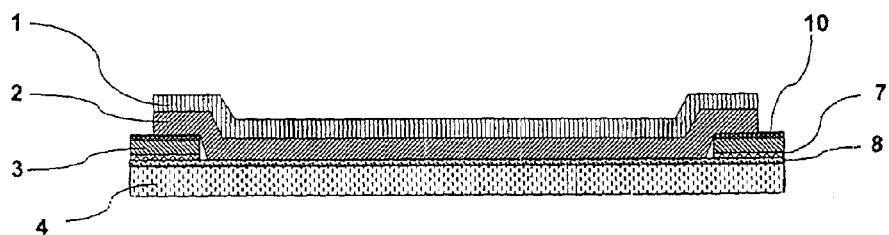
FIG. 8a
FIG. 8b
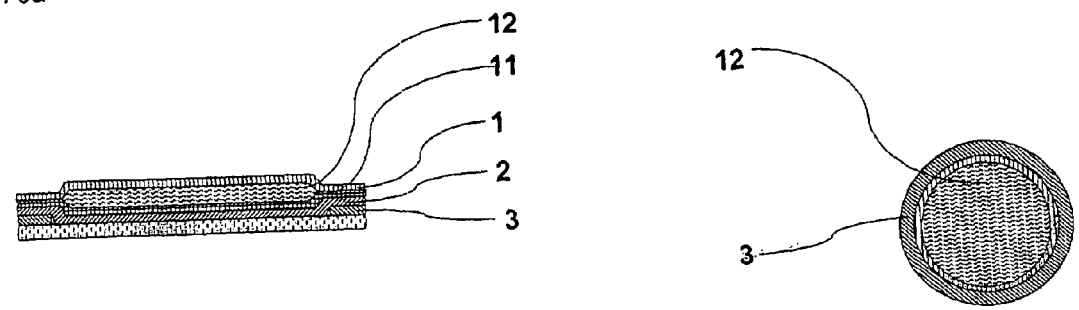

MEDICINAL PATCH THAT LEAVES LESS ADHESIVE RESIDUE WHEN REMOVED

CROSS-REFERENCE

The present invention is also described in U.S. Provisional Patent Application 60/558,033, filed Mar. 31, 2004, which provides the basis for a claim of priority under 35 U.S.C. 119.

BACKGROUND OF THE INVENTION

Medicinal patches usually leave behind a distinctive dirt rim, dirt ring or dark ring on the skin after being removed from the skin. This phenomenon becomes more important depending on the application duration and takes an especially problematic form, when the patch is worn for longer than 3 and up to 7 days. This situation especially occurs with an effective-ingredient transdermal patch, which is often applied for seven days during hormone substitution or hormonal contraception.

The dirt rim essentially forms by adherence of textile fibers, dirt and skin particles on the exposed cut edge of the adhesive layer. The adhesive layer can absorb particles, even by adhesive flow, according to the boundary surface energy and the adhesive properties. This is especially promoted by mechanical action on patches that are carried on the skin for a long time, in which adhesive material issues from the edge, which increases the adherence of particles at the dirty edge. The release of the patch starting from the edge after a long wearing time provides further surfaces on which dirt can be deposited.

A more or less large part of the dirt rim or ring remains on the skin after removal of the patch. It may be mechanically mostly poorly rubbed off and disappear after several days of the usual body care.

Of course improvements can be obtained by increasing the cohesion of the medicinal adhesive, for example by mixing in long-chain polymers or by chemical cross-linking. Frequently however the long time adherence is reduced with increased cohesion and reduced plasticity. Only a partially free-flowing adhesive with aggressive adhesive properties can guarantee adherence on the skin for up to one week. In this area of conflicting requirements for medicinal adhesives it is currently not possible to avoid formation of cosmetically interfering dirt rims or rings during long duration application.

SUMMARY OF THE INVENTION

It is an object of the present invention to completely avoid or largely eliminate the problem of dirt rim or dirt ring formation by a means other than optimizing the medicinal adhesive.

To a surprisingly great extent the formation of dirt rims or dirt rings after removal of a medicinal patch can be partially or even completely avoided, when the edge region of the medicinal patch is not adhering. The interior edge of the adhesive surface is largely protected from contact with dirt and fiber by an adhesive-free edge provided on all sides of the patch or completely around the patch.

Furthermore even more surprisingly this protection of the adhesive edge in connection with mechanical strengthening of this edge zone improves the long time adhesive of the patch, since the mechanical loosening of the patch caused by rubbing on cloths and lifting of the patch edge is reduced or delayed.

One skilled in the art would have expected that a patch that does not adhere at its edges would be rubbed off even faster by contact with cloths or other mechanical stresses.

DETAILED DESCRIPTION OF THE INVENTION

Surprisingly the inventor has established that the wearing comfort of medicinal patches is improved when the edge region is non-adhering. This can be realized by introduction of an additional layer in the edge region of the patch in a most suitable manner during production. This is preferably accomplished by introducing a small foil integrated in the patch in the edge region, which is designated as the edge foil.

This edge foil is located between the skin-side adhesive layer of the patch and the skin, so that contact of the adhesive with the skin in this edge region is prevented.

In the case of patches containing an effective ingredient the edge foil is preferably made of a material, which is practically impermeable for the effective ingredient or ingredients. Otherwise an effective ingredient delivery occurs in the edge region like a patch on the skin, which is not desirable because of the construction-dependent poor reproducibility of the contact with the skin in the edge region and also because the effective ingredient delivery through the edge foil necessarily occurs with different kinetics from the delivery through the central adhesive layer of the patch. For this reason the materials suitable for the edge foil include polyethylene terephthalate (PET), polyvinyl chloride (PVC), polyvinylidene chloride (PVDC) or polyvinyl chloride-polyvinylidene chloride copolymer (e.g. SARAN® from Dow Chemical Company) and polyacryl nitrile (e.g. BAREX® from BP Chemicals). PET (e.g. HOSTAPHAN® from Mitsubishi) is especially preferred because of the many commercially available types, especially very thin foils, of this material.

The residual effective ingredient delivery rate through the edge region should preferably be a factor of ten less, especially preferably at least a factor of 100, less than the effective ingredient delivery rate over the adhering interior region of the patch.

An optimal area of the edge region should be determined: too large a width leads to an edge region, which is easily turned up and pulled up, which leads to premature removal of the patch. If the edge region is too small in contrast it is difficult to produce the patch with sufficient symmetry and reproducibility and only insufficient protection of the interior adhesive surface from particle contamination from the exterior is provided.

It was found that the edge width should be in a range from 0.5 to 5 mm, preferably from 0.75 to 3 mm and especially preferably in a range from 1 to 1.5 mm. The optimal value depends however on the size of the patch and the curvature radius of its contour line. Larger patches with greater radii can also be provided with wider edge regions. The ideal value of 1 to 1.5 mm width is especially applicable to patches of a size from 5 to 25 $cm^2$, which have a circular, oval or rectangular shape.

In individual embodiments it can be important to make the width of the edge region variable along the contour line of the patch, e.g. wider in regions of smaller curvature radii, i.e. smaller with tight radii, because the danger of mechanically turning up of the edge with contact with wearing apparel is especially great when the curvature is tight.

The thickness of the edge foil similarly should be optimized so that it is not too thin and not too thick. A foil that is too thick reduces the wearing comfort of the patch due to mechanical loads on the skin according to the foil material because of its rigidity, even with narrow edge region widths. In contrast an edge foil that is too thin does not have sufficient strength, so that the contact of the edge region with the skin is easily lost and the edge region is easily turned up, e.g. by giving way or rolling in at the edge of the patch.

A material of suitable thickness of course provides the required shape stability, but does not impair the mechanical wearing comfort to any detectable extent.

In the case of polyester foils (PET) a thickness of 9 to 75 μm, preferably from 15 or 19 to 50 μm and especially preferably about 36 am, has been established as especially suitable. However the polyester edge foil can have a thickness from 6 to 150 μm.

In preferred embodiments it was found that a repellant coating on a surface of the edge foil facing the skin acts advantageously, since it prevents flow or creep of the adherent adhesive material during storage and during application to the skin. The edge region thus remains free of adhesive longer and formation of dirt ring or dirt rim is further reduced.

In the case of adhesive material based on polyacrylates or hydrocarbon materials (e.g. polyisobutylene) siliconization is suitable to provide a repellant coating. In the case of adhesive material based on silicon the repellant coating should be based on special fluorinated polymers, which are known in the art of release lining for this sort of adhesive. Preferred layer thickness values are the same as for the edge foils based on polyester.

This repellant coating should have a small mechanical rub off tendency for patches for long duration applications of 3 to 7 days, in order to guarantee a long retention time or hold on the skin. The problem of rub-off is known to those skilled in the art in the siliconization field and different methods and products are available for reducing it. In order to make a dirt-minimizing edge region more easily observable for a user, the invention advantageously provides the edge region with colors or transparency so that it differs from the remaining surface of the patch. This can happen, for example, by lacquering or metallizing the edge foil, preferably by aluminum vapor deposition on an edge foil surface facing the skin. Alternatively the visual emphasizing of the edge zone can occur by partially imprinting the rear layer of the patch.

There are no special requirements for the rear layer of the medicinal patch according to the invention beyond the usual requirements in this field. Polyester foils (PET, e.g. HOSTAPHAN® from Mitsubishi), polyethylene foils (e.g. CoTrane 9720 from 3M) or multi-layer laminates, which contain these materials, are used.

The adhesive layer can comprise one or several layers, which can be the same or different composition. Preferably the one or two-layer system contains at least one pharmaceutically effective ingredient in one or both layers. However the invention expressly does not concern medicinal patches that do not contain an effective ingredient, for example patches or bandages for fixing a catheter and for care and healing of a wound or cut.

Pressure sensitive adhesives based on polyacrylates, hydrocarbons or silicones and mixtures of them, which are known to those skilled in the art from the fields of medicinal patches and transdermal therapeutic systems, are suitable.

Because of the structure according to the invention which prevents dirt ring formation strongly adhesive and slightly cohesive are generally used, which would not be otherwise acceptable because of the discharge of adhesive mass at the patch edge during storage and/or application. These types of formulations are based, for example, on uncross-linked polyacrylate adhesives (e.g. Durotak 387-2051, Durotak 387-2287), un-cross-linked silicone adhesives with spontaneous adherence/tackiness (e.g. Dow Corning BIO-PSA® 430X or 460X with x=1, 2, 3) or hydrocarbons (e.g. more than 20% OPPANOL® B10 from the firm Beiersdorf). The effective ingredient portion of the patch can be formulated in a sort of reservoir system with a semisolid or liquid effective ingredient reservoir.

Usually all foils and coated papers are suitable as release liners for medicinal patches and transdermal therapeutic systems. There are no special requirements for the release liners.

The release liner can be the same size and shape as the patch applied to it or can protrude laterally from it. To make application of the patch easier application assisting elements can be punched in the release liner.

BRIEF DESCRIPTION OF THE DRAWING

The objects, features and advantages of the invention will now be illustrated in more detail with the aid of the following description of the preferred embodiments, with reference to the accompanying figures in which:

FIG. 1b is plan view of the patch shown in FIG. 1a;

FIG. 2b is plan view of the patch shown in FIG. 2a;

FIG. 3b is plan view of the patch shown in FIG. 3a;

FIG. 5 is a cross-sectional view of an additional preferred embodiment of a type A medicinal patch according to the invention;

FIG. 6 is a cross-sectional view of a further preferred embodiment of a type A medicinal patch according to the invention;

FIG. 7 is a cross-sectional view of a further preferred embodiment of a type C medicinal patch according to the invention;

FIG. 8a is a cross-sectional view of an effective-ingredient containing patch according to the invention, which operates like a reservoir system; and FIG. 8b is a plan view of the patch shown in FIG. 8a.

DESCRIPTION OF THE PREFERRED EMBODIMENTS

Figure 1A:
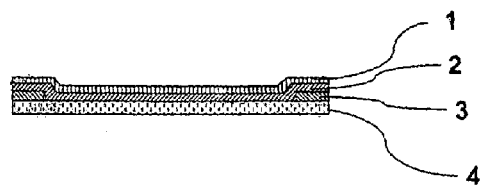
FIG. 1a is a cross-sectional view of a first embodiment of a medicinal patch according to the invention with the simplest structure, which is designated type A.
Figure 1B:
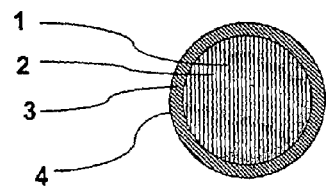
Figure 2A:
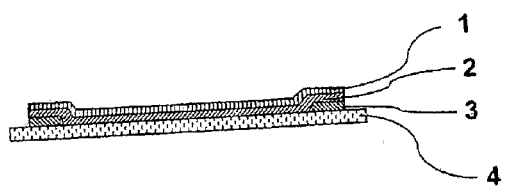
FIG. 2a is a cross-sectional view of a second embodiment of a medicinal patch according to the invention with a different release liner from that of FIG. 1a that extends beyond the edge of the remaining layers, which is called type B.
Figure 2B:
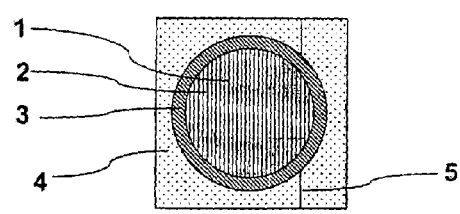
Figure 3A:
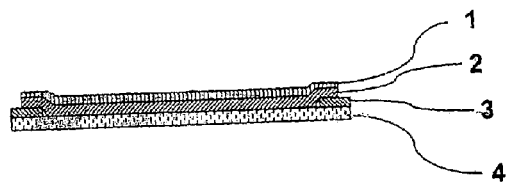
FIG. 3a is a cross-sectional view of a third embodiment of a medicinal patch according to the invention designated type C with a different edge foil from that of previous embodiments, which extends laterally beyond the edges of the backing layer and the adhesive matrix layer.
Figure 3B:
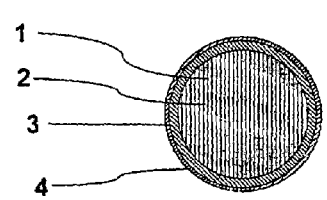

A type A medicinal patch is shown in FIG. 1a and FIG. 1b. Type A medicinal patches have the simplest possible structure according to the invention. At least one effective-ingredient adhesive matrix layer 2 is applied to a backing layer 1. The at least one effective-ingredient adhesive matrix layer 2 is followed by an edge foil 3 applied on the edge region. A removable protective foil (release liner) 4 is provided over the edge foil 3 and the adhesive matrix layer 2. The release liner 4 does not extend laterally beyond the edges of the other layers. This embodiment is a matter of a complete punch out or punch through system.

Figure 4:
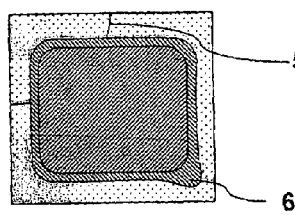
FIG. 4 is a cross-sectional view of an additional embodiment of a type B medicinal patch according to the invention.

In the optional type B embodiment shown in FIG. 4 a slot or cut 5 is provided in the release liner 4, along which one part of the release liner can be removed before the patch is first applied. After the first part of the release line 4 is removed and the patch is partially applied, the second half of the release liner can then be removed and the patch can then be completely applied to the surface of the skin.

A strap-shaped protrusion 6 of plastic foil or film is provided extending from the edge foil or outer region to make the later removal of the patch from the skin easier (see FIG. 4). At the end of the application time the patch can be easily grasped at this protrusion and pulled off.

In the case of the embodiment shown in FIG. 5 the surface of the edge foil 3 bearing on the release liner has a repellant coating 7 on the side opposite from the adhesive matrix layer 2. The surface of the release liner 4 facing the remaining layers of the patch is similarly coated with a repellant layer, which is the same or different from the repellant coating 7 on the edge foil 3.

In the embodiment shown in FIG. 6 the surface of the edge foil 3 bearing on the release liner has a repellant coating 7 on the side opposite from the adhesive matrix layer 2. The surface of the edge foil 3 facing the matrix layer 2 of the patch has an aluminization 9 in order to easily distinguish the outer region of the interior region or the rest of the patch.

In the embodiment shown in FIG. 7 the surface of the edge foil 3 bearing on the release liner has a repellant coating 7 on the side opposite from the adhesive matrix layer 2. The surface of the edge foil 3 facing the matrix layer 2 of the patch has a repellant coating 10. The surface of the release liner 4 facing the remaining layers of the patch again has a repellant coating 8, which can be the same or different from the repellant coatings 7, 10 of the edge foil. The coatings 7, 10 of the edge foil 3 can themselves be the same or different.

The separating force for removing the adhesive matrix layer 2 from the coating 8 of the release liner 4 is preferably larger than the separating force for removing the adhesive matrix layer 2 from the coating 10 on the edge foil, so that in the manufacturing process the adherent matrix layer 2 can be removed from the coating 10 of the edge foil, without release from the coating 8 of the release liner 4.

FIGS. 8a and 8b illustrate the transfer of the concept according to the invention to an effective ingredient-containing patch of the reservoir system type. A liquid or semisolid effective ingredient reservoir 12 is arranged between a backing layer 1 and a hot-sealed intervening layer 11, which can be embodied as a control membrane for controlling effective ingredient delivery. Otherwise this system corresponds to the Type A embodiment shown in FIGS. 1a and 1b.

In order to manufacture the patches with a non-adherent region in the outer region the insertion of an edge foil along the patch edge by processing methods is preferred. In the following the essential manufacturing steps for the base types A, B and C of the patch are described. Types D to G may be made by variations in starting material and process steps that are obvious to one skilled in the art.

One method for making a medicinal patch of type A or B according to the invention, includes making a preliminary laminate for the interior region, which comprises a backing layer, at least one effective ingredient-containing adhesive layer and an optional, but preferable, removable protective foil and the use of an edge foil, preferably coated with a repellant coating, for the outer region. This method includes the following steps:

a) a section or piece corresponding to the shape of the later-formed interior region is punched out from a foil provided for the outer region, thus forming the edge foil and the punched out section or piece, which is then discarded;

b) the edge foil formed in step a) is assembled together with a release liner of the patch to form a first laminate, so that in the case of optional repellant coating of surfaces of the edge foil and the release liner a repellant surface of the edge foil is in contact with a repellant surface of the release liner;

c) forming a second laminate for the interior region comprising a backing layer and at least one adhesive matrix layer, from which any protective foil provided thereon earlier during manufacturing is removed;

d) combining the first laminate with the second laminate so that an adherent side of the second laminate is in contact with the first laminate, wherein the adherent side of the second laminate is placed on uncoated surfaces of the edge foil for the outer region and directly over a punched out opening provided in the edge foil in step a) and also so that the adherent side of the second laminate is in contact with an optionally repellant coated surface of the release liner, so as to form a combined patch laminate; and e) punching the combined patch laminate to form an outer contour line of a finished patch, which extends around the punched out opening in the edge foil for the outer region, so that the outer contour line is spaced from the opening by a distance equal to the width of the outer region.

When a medicinal patch of type A is being made, all the layers of the combined patch laminate are punched through in order to form the outer contour line and the outer contour line of the release liner does not extend beyond the outer contour line of the remaining layers of the patch.

The method of making the medicinal patch of type B is the same as for the medicinal patch of type A, except that all layers of the combined patch laminate are not punched through, but instead through all layers, except for the release liner, are punched through. After that excess laminate material is removed from the release liner and thrown out before the final shape or outer contour line of the release liner is punched out or cut so that the release linear extends beyond the outer edges of the remaining layers of the patch.

The method of making the medicinal patch of type C according to the invention, includes first making a preliminary laminate for an interior region of the patch, which comprises a rear protective layer, at least one effective ingredient-containing adhesive layer and an optional removable protective foil and also using an edge foil for an outer region of the patch. This method comprises the following steps of:

a) punching out a section or piece corresponding to a shape of the interior region from a foil provided for the outer region, thus forming the edge foil and the section or piece, which is then discarded as waste;

b) assembling the edge foil formed in step a) together with a release liner for the patch to form a first laminate, so that in the case of optional repellant coating of surfaces of the edge foil and release liner a repellant surface of the edge foil is in contact with a repellant surface of the release liner;

c) forming a second laminate for the interior region comprising a backing layer and at least one adhesive matrix layer, from which any protective foil provided thereon earlier during manufacturing is removed;

d) combining the first laminate with the second laminate so that an adherent side of the second laminate is in contact with the first laminate, wherein the adherent side of the second laminate is placed on uncoated surfaces of the edge foil for the outer region and directly over a punched out opening in the edge foil formed in step a) and also so that the adherent side of the second laminate is in contact with an optionally repellant coated surface of the release liner, so as to form a combined patch laminate;

e) punching through the backing layer and the at least one adhesive matrix layer to form an inner contour line of the patch, which extends around the punched out opening in the edge foil for the outer region formed in step a) at a predetermined distance from the punched out opening;

f) removing excess laminate material on the release liner from the backing layer and the at least one adhesive matrix layer and disposing the excess laminate material; and g) punching through the edge foil and the release liner to form an outer contour line so that the outer contour line extends around the punched out opening in the edge foil for the outer region, so that the outer contour line is spaced from the opening by a distance equal to a width of the outer region.

The following example is illustrative of the patch according to the invention, but its details should not be considered as limiting the scope of the appended claims.

EXAMPLE

Patch Composition:
Patch Backing Layer:
Polyethylene foil CoTran 9720 (from 3M)

| Adhesive Matrix: Layer strength 100 g/m² | Parts (dry) |
|---|---|
| Ethinyl estradiol | 0.6 |
| Gestoden | 1.9 |
| MA73A | 97.5 |
| Total | 100.00 |

Edge Foil in Outer Region:

Polyethylene terephthalate (PET) 36 μm (HOS-TAPHAN®) RN 36, one side siliconized (Laufenberg).

Release Liner:

Scotch Pak 9742 (3M)=117 μm polyester foil, one side coated with a fluoro-polymer.

The making of exemplary systems comprising the patch according to the invention starts with the effective ingredient adhesive matrix. Both effective ingredients, ethinyl estradiol and gestagen, are dissolved in an adhesive solution MA73A (Adhesives Research, adhesive based on polyisobutylene with an adherent resin additive based on hydrated Colophonium ester). This solution is coated with a manually operated film drawing frame (Erichsen Co.) on a siliconized polyester foil (protective foil) with a layer thickness of 500 μm. This film is dried for 10 minutes drying time in a laboratory hood and then dried at room temperature for a still further 30 minutes at 60° C. in a drying unit. The dried film has a thickness of about 100 g/m². If necessary the gap height must be adjusted during coating until the desired surface weight is reached. The dried film is covered with a backing layer of CoTran 9720. A circular opening of 10 cm² area is punched out in the edge foil. The edge foil is subsequently placed on the release liner foil with the siliconized side down. The siliconized side of the release layer is facing upward.

Then the protective foil is removed from the adhesive matrix and the exposed adhesive surface is bonded to the edge foil. The adhesive layer is permanently bonded with the unsiliconized surface of the edge foil. Because of the opening in the edge foil formed during the punching out an easily releasable bond is formed between the adhesive layer and the siliconized surface of the release layer.

Subsequently an 11.5 cm² circular TTS patch is punched out of the composite laminate formed by the above steps. This outer contour line is symmetric around the circular opening punched out of the edge foil, which is 10 cm². Thus the edge zone has a width of about 1 mm.

The disclosure in U.S. Provisional Patent Application 60/558,003, filed Mar. 31, 2004, is incorporated here by reference. This German Patent Application describes the invention described hereinabove and claimed in the claims appended hereinbelow and provides the basis for a claim of priority for the instant invention.

While the invention has been illustrated and described as embodied in a medicinal path with reduced adhesive adherence or dirtless patch, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A method of making a medicinal patch of type A or B includes first making a preliminary laminate for an interior region of the patch, said preliminary laminate comprising a rear protective layer, at least one effective ingredient-containing adhesive layer and an optional removable protective foil and also providing an edge foil for an outer region of the patch, said method comprising the steps of:

a) punching out a section or piece corresponding to a shape of the interior region from a foil provided for the outer region, thus forming the edge foil and the section or piece, said section or piece then being discarded as waste;

b) assembling the edge foil formed in step a) together with a release liner for the patch to form a first laminate, so that in the case of optional repellant coating of surfaces of the edge foil and the release liner a repellant surface of the edge foil is in contact with a repellant surface of the release liner;

c) forming a second laminate for the interior region comprising a backing layer and at least one adhesive matrix layer, from which any protective foil provided thereon earlier during manufacturing is removed;

d) combining the first laminate with the second laminate so that an adherent side of the second laminate is in contact with the first laminate, wherein the adherent side of the second laminate is placed on uncoated surfaces of the edge foil for the outer region and directly over a punched out opening provided in the edge foil in step a) and also so that the adherent side of the second laminate is in contact with an optionally repellant coated surface of the release liner, so as to form a combined patch laminate; and e) punching the combined patch laminate to form an outer contour line of a finished patch, which extends around the punched out opening in the edge foil for the outer region, said outer contour line being spaced from the opening by a distance equal to a width of the outer region.

2. The method as defined in claim 1, wherein all layers of the combined patch laminate are punched through in said punching, in order to form the outer contour line, and an outer edge of the release liner does not extend beyond outer edges of remaining layers of the patch.

3. A method of making a medicinal patch includes first making a preliminary laminate for an interior region of the patch, said preliminary laminate comprising a rear protective layer, at least one effective ingredient-containing adhesive layer and an optional removable protective foil and also providing an edge foil for an outer region of the patch, said method comprising the steps of:
   a) punching out a section or piece corresponding to a shape of the interior region from a foil provided for the outer region, thus forming the edge foil and the section or piece, said section or piece then being discarded as waste;
   b) assembling the edge foil formed in step a) together with a release liner for the patch to form a first laminate, so that in the case of optional repellant coating of surfaces of the edge foil and the release liner a repellant surface of the edge foil is in contact with a repellant surface of the release liner;
   c) forming a second laminate for the interior region comprising a backing layer and at least one adhesive matrix layer, from which any protective foil provided thereon earlier during manufacturing is removed;
   d) combining the first laminate with the second laminate so that an adherent side of the second laminate is in contact with the first laminate, wherein the adherent side of the second laminate is placed on uncoated surfaces of the edge foil for the outer region and directly over a punched out opening provided in the edge foil in step a) and also so that the adherent side of the second laminate is in contact with an optionally repellant coated surface of the release liner, so as to form a combined patch laminate; and
   e) punching the combined patch laminate to form an outer contour line of a finished patch, which extends around the punched out opening in the edge foil for the outer region, said outer contour line being spaced from the opening by a distance equal to a width of the outer region;
wherein all layers of the combined patch laminate are punched through in said punching, except that the release liner is not punched through, excess laminate material is removed from the release liner and thrown out and then an outer contour line of the release liner is punched out or cut out so that an outer edge of the release linear extends beyond outer edges of remaining layers of the patch.

4. A method of making a medicinal patch includes first making a preliminary laminate for an interior region of the patch, said preliminary laminate comprising a rear protective layer, at least one effective ingredient-containing adhesive layer and an optional removable protective foil and also providing an edge foil for an outer region of the patch, said method comprising the steps of:
   a) punching out a section or piece corresponding to a shape of the interior region from a foil provided for the outer region, thus forming the edge foil and the section or piece, said section or piece then being discarded as waste;
   b) assembling the edge foil formed in step a) together with a release liner for the patch to form a first laminate, so that in the case of optional repellant coating of surfaces of the edge foil and the release liner a repellant surface of the edge foil is in contact with a repellant surface of the release liner;
   c) forming a second laminate for the interior region comprising a backing layer and at least one adhesive matrix layer, from which any protective foil provided thereon earlier during manufacturing is removed;
   d) combining the first laminate with the second laminate so that an adherent side of the second laminate is in contact with the first laminate, wherein the adherent side of the second laminate is placed on uncoated surfaces of the edge foil for the outer region and directly over a punched out opening provided in the edge foil in step a) and also so that the adherent side of the second laminate is in contact with an optionally repellant coated surface of the release liner, so as to form a combined patch laminate; and
   e) punching the combined patch laminate to form an outer contour line of a finished patch, which extends around the punched out opening in the edge foil for the outer region, said outer contour line being spaced from the opening by a distance equal to a width of the outer region; wherein the edge foil and the release liner are each provided with said repellent surface.

5. A method of making a medicinal patch includes first making a preliminary laminate for an interior region of the patch, said preliminary laminate comprising a rear protective layer, at least one effective ingredient-containing adhesive layer and an optional removable protective foil and also providing an edge foil for an outer region of the patch, said method comprising the steps of:
   a) punching out a section or piece corresponding to a shape of the interior region from a foil provided for the outer region, thus forming the edge foil and the section or piece, said section or piece then being discarded as waste;
   b) assembling the edge foil formed in step a) together with a release liner for the patch to form a first laminate, so that in the case of optional repellant coating of surfaces of the edge foil and release liner a repellant surface of the edge foil is in contact with a repellant surface of the release liner;
   c) forming a second laminate for the interior region comprising a backing layer and at least one adhesive matrix layer, from which any protective foil provided thereon earlier during manufacturing is removed;
   d) combining the first laminate with the second laminate so that an adherent side of the second laminate is in contact with the first laminate, wherein the adherent side of the second laminate is placed on uncoated surfaces of the edge foil for the outer region and directly over a punched out opening in the edge foil formed in step a) and also so that the adherent side of the second laminate is in contact with an optionally repellant coated surface of the release liner, so as to form a combined patch laminate;
   e) punching through the backing layer and the at least one adhesive matrix layer to form an inner contour line of the patch, which extends around the punched out opening in the edge foil for the outer region formed in step a) at a predetermined distance from the punched out opening;
   f) removing excess laminate material on the release liner from the backing layer and the at least one adhesive matrix layer and disposing the excess laminate material; and
   g) punching through the edge foil and the release liner to form an outer contour line so that the outer contour line extends around the punched out opening in the edge foil for the outer region, said outer contour line being spaced from the opening by a distance equal to a width of the outer region.

* * * * *